US012611120B2

(12) United States Patent
Cathelain

(10) Patent No.: US 12,611,120 B2
(45) Date of Patent: Apr. 28, 2026

(54) BALLISTOCARDIOGRAPHY DEVICE AND METHOD

(71) Applicants:PARIS SCIENCES ET LETTRES, Paris (FR); ÉCOLE PRATIQUE DES HAUTES ÉTUDES, Paris (FR)

(72) Inventor: Guillaume Cathelain, Issy les Moulineaux (FR)

( * ) Notice: Subject to any disclaimer, the term of this patent is extended or adjusted under 35 U.S.C. 154(b) by 855 days.

(21) Appl. No.: 17/906,422

(22) PCT Filed: Mar. 16, 2021

(86) PCT No.: PCT/EP2021/056667
§ 371 (c)(1),
(2) Date: Sep. 15, 2022

(87) PCT Pub. No.: WO2021/185825
PCT Pub. Date: Sep. 23, 2021

(65) Prior Publication Data
US 2023/0110553 A1     Apr. 13, 2023

(30) Foreign Application Priority Data

Mar. 16, 2020    (FR) ..................................... 2002547

(51) Int. Cl.
*A61B 5/11*          (2006.01)
*A61B 5/00*          (2006.01)
(52) U.S. Cl.
CPC .......... *A61B 5/1102* (2013.01); *A61B 5/6892* (2013.01); *A61B 5/7207* (2013.01);
(Continued)
(58) Field of Classification Search
CPC ... A61B 5/1102; A61B 5/6892; A61B 5/7207; A61B 5/7225; A61B 5/725;
(Continued)

(56) References Cited

U.S. PATENT DOCUMENTS

2006/0186951 A1* 8/2006 Ohannaidh ........ H03H 11/1286
327/552
2009/0054742 A1 2/2009 Kaminska et al.
(Continued)

FOREIGN PATENT DOCUMENTS

WO      WO-2017127944 A1 * 8/2017 ............. A61B 17/29

OTHER PUBLICATIONS

Ostchega, Yechiam et al., "Resting Pulse Rate Reference Data for Children, Adolescents, and Adults: United States, 1999-2008," Natl Health Stat Report. Aug. 24, 2011;(41):1-16. PMID: 21905522 (Year: 2011).*
Kriz, J., Seba, P. "Force plate monitoring of human hemodynamics." Nonlinear Biomed Phys 2, 1 (2008). https://doi.org/10.1186/1753-4631-2-1 (Year: 2008).*
ISR; European Patent Office; Jul. 6, 2021.
Postolache O et al: Vital Signs Monitoring System Based on EMFI Sensors and Wavelet Analysis; May 1, 2007.

*Primary Examiner* — Andrew Schechter
*Assistant Examiner* — Ethan Wesley Edwards
(74) *Attorney, Agent, or Firm* — Patshegen IP; Moshe Pinchas

(57)          ABSTRACT

A ballistocardiography device comprises:
  a support for a person,
  a plurality of pressure or acceleration sensors each providing an analogue signal representative of a pressure or an acceleration measured at a point on the support or on the body of the person,
  a multiplexer (41) configured to receive a plurality of analogue signals from sensors and to output a signal successively representative of the input signals and
  an operational amplifier (52) having one input (57) connected to the output of the multiplexer and provided, on its other input, with a mixed filter comprising an analogue-to-digital converter (53) converting the signal coming out of the multiplexer into digital data, a digital filter (54) acting on the digital data and a digital-to-analogue converter (55) converting the filtered digital
(Continued)

data into an analogue signal that is fed into the other input (58) of the operational amplifier.

10 Claims, 10 Drawing Sheets

(52) U.S. Cl.
CPC ............ *A61B 5/7225* (2013.01); *A61B 5/725* (2013.01); *A61B 5/7257* (2013.01); *A61B 2505/05* (2013.01); *A61B 2562/0219* (2013.01); *A61B 2562/0247* (2013.01); *A61B 2562/046* (2013.01); *A61B 2562/06* (2013.01)

(58) Field of Classification Search
CPC .............. A61B 5/7257; A61B 2505/05; A61B 2562/0219; A61B 2562/0247; A61B 2562/046; A61B 2562/06
See application file for complete search history.

(56) References Cited

U.S. PATENT DOCUMENTS

| | | | |
|---|---|---|---|
| 2010/0054496 A1* | 3/2010 | Williams ................. | H04R 3/02 |
| | | | 381/93 |
| 2014/0142451 A1* | 5/2014 | Kim ..................... | A61B 5/1171 |
| | | | 600/526 |
| 2016/0157777 A1* | 6/2016 | Attal ...................... | A61B 5/291 |
| | | | 600/383 |
| 2017/0156632 A1* | 6/2017 | Swiston ................. | A61B 5/073 |
| 2018/0125256 A1* | 5/2018 | Tsern ................... | A47C 27/083 |
| 2022/0140834 A1* | 5/2022 | Wang ..................... | H03M 1/02 |
| | | | 341/141 |

OTHER PUBLICATIONS

Rikky Muller et al: IEEE Journal of Solid State Circuits, IEEE, USA; Jan. 1, 2012.
Mohammad Mojarradi et al: NASA Tech Briefs; Sep. 1, 2004.

* cited by examiner

80

90

BALLISTOCARDIOGRAPHY DEVICE AND METHOD

TECHNICAL FIELD OF THE INVENTION

The present invention relates to a ballistocardiography device and method. It applies, in particular, to ballistocardiography, i.e. the non-intrusive measurement of mechanical cardiac activity.

STATE OF THE ART

Ballistocardiography (BCG) is a method of monitoring the cardiac rhythm without contact, which makes it possible to measure the patient's vital signs and reduce his pain and discomfort related to monitoring. It uses an accelerometer placed on the side of the mattress. Because the amplitude of the signal is very small, the front-end electronic circuit conditioning the signal needs a high amplification gain and is therefore very sensitive to the drift of the direct component and to the background noise.

However, the known analogue filters are slow to stabilize, and the patient plus the bed form a mechanical mass-spring system that generates noise at its resonance frequency. As a result, the signal of the ballistocardiogram is likely to saturate for several seconds each time the patient moves.

In the prior state of the art, an analogue amplification is required to obtain good detection performance. It is therefore very sensitive to the drift of the direct component that is produced when the patient changes position, for example from the position lying on the stomach to the position lying on the back, and must be filtered. However, for measuring the respiratory activity whose low-frequency components are approximately 0.1 Hz, the normal high-pass filters are slow to stabilize and the signal of the ballistocardiogram can saturate during several tens of seconds. The addition of non-linear components, for example switching diodes in the feedback loop of the amplifier, can help to reduce the stabilization time of the amplifier, i.e. the length of time before the end of saturation, for just a few seconds. In addition, the patient and his bed can be considered as a mass-spring system that generates noise at its resonance frequency. Surrounding noises, for example the steps of nurses, ventilation units, or during transport in the paediatric intensive care unit, can also occur. For the same reasons of saturation, these repetitive noises must be filtered, otherwise the monitoring time may be reduced.

PRESENTATION OF THE INVENTION

The present invention aims to remedy all or part of these drawbacks.

To this end, according to a first aspect, the present invention relates to a ballistocardiography device, which comprises:
- a support for a person;
- a plurality of pressure or acceleration sensors each providing an analogue signal representative of a pressure or an acceleration measured at a point on the support or on the body of the person;
- a multiplexer configured to receive a plurality of analogue signals from sensors and to output a signal successively representative of the input signals; and
- an amplifier having one input connected to the output of the multiplexer and provided, on its other input, with a mixed filter comprising an analogue-to-digital converter converting the signal coming out of the multiplexer into digital data, a digital filter acting on the digital data and a digital-to-analogue converter ("DAC") converting the filtered digital data into an analogue signal that is fed into this other input of the amplifier.

Thanks to these provisions, the state and coefficients of the digital filter can be modified sufficiently quickly such that each sensor is successively associated with specific digital filtering. The device can therefore utilize hundreds, even thousands, of sensors and perform a finer analysis of the data collected at low cost. In addition, the amplification rate can be higher, because the direct component can be better filtered. Each of the signals to be processed can therefore be of better quality and further improve the analysis carried out. Lastly, each digital filter can have a higher order than analogue filters. The invention therefore makes it possible to carry out a more precise cardiac mapping than the known ballistocardiography devices.

In some embodiments, the device comprises, for each sensor, a memory of the digital data output successively from the analogue-to-digital converter when the signal from this sensor is supplied on output from the multiplexer, and the filter comprises a processor, which processes the data memorized successively to apply filtering of this data and supply an item of digital data that is converted by the digital-to-analogue converter.

Thanks to these provisions, the signals from the various sensors are processed independently, but taking into account their evolution to eliminate the drift of the direct component and stabilize the filtering applied.

In some embodiments, the digital filter is a cascade of biquad filters, also known as biquad cascade filters.

This is an effective filter, very easy to implement in embedded systems such as microcontrollers.

In some embodiments, the sampling frequency of the analogue-to-digital converter is equal to the number of sensors multiplied by a number between 128 and 512.

Thanks to these provisions, the heart and breathing rates are detected accurately.

In some embodiments, the plurality of sensors forms at least one matrix of pressure sensors.

Thanks to these provisions, hundreds, even thousands, of sensors are utilized, and the ballistocardiography or cardio-respiratory mapping has a high resolution.

In some embodiments, the gain of the amplifier is greater than 10.

The vibrations detected are therefore of very low amplitude, which increases the precision of the device.

According to a second aspect, the present invention relates to an application of a device that is the subject of the invention for monitoring a patient during a surgical operation.

According to a third aspect, the present invention relates to an application of a device that is the subject of the invention for viewing the pulse wave and the contraction of the ventricles.

This application makes it possible to produce a simplified scanner for vital functions, for example viewing the pulse wave and contraction of the ventricles, at lower cost and in real time during an operation or while monitoring a patient.

According to a fourth aspect, the present invention relates to a ballistocardiography method utilizing a device that is the subject of the present invention, which comprises the following steps:
- a plurality of pressure or acceleration captures at different points of a support for a person providing, for each capture point, an analogue signal representative of a pressure or an acceleration measured at a point on the support or on the body of the person;

a multiplexing of the plurality of analogue signals; and an amplification of the multiplexed signal from which is subtracted a signal filtered by a mixed filter comprising a mixed filter comprising an analogue-to-digital converter converting the signal coming out of the multiplexer into digital data, a digital filter acting on the digital data and a digital-to-analogue converter converting the filtered digital data into an analogue signal.

In some embodiments, the method that is the subject of the invention also comprises a step of estimating the direct component, and a step of initializing the filter with the estimated direct component.

Thanks to these provisions, the stabilization time of the filtered signal is much reduced.

In some embodiments, the method that is the subject of the invention also comprises:

a step of detecting a vibration in the amplified signal;

a step of segmenting the vibration signal;

a step of transforming segments of the signal in the frequency domain;

a step of obtaining a maximum of the signal in the frequency domain;

a step of configuring a notch filter comprising the maximum obtained; and a step of filtering the amplified signal with the notch filter.

Thanks to these provisions, the noise, for example generated by the patient's movements, is extracted from the signal processed and viewed.

As the particular aims, advantages and features of the method and applications that are the subjects of the present invention are similar to those of the device that is the subject of the present invention, they are not repeated here.

BRIEF DESCRIPTION OF THE FIGURES

Other advantages, aims and particular features of the invention will become apparent from the non-limiting description that follows of at least one particular embodiment of the device and method that are the subjects of the present invention, with reference to drawings included in an appendix, wherein.

DESCRIPTION OF EMBODIMENTS

The present description is given in a non-limiting way, in which each characteristic of an embodiment can be combined with any other characteristic of any other embodiment in an advantageous way.

Note that the figures are not to scale.

Throughout the description the terms "processor" and "microcontroller" will be used interchangeably.

Figure 1:
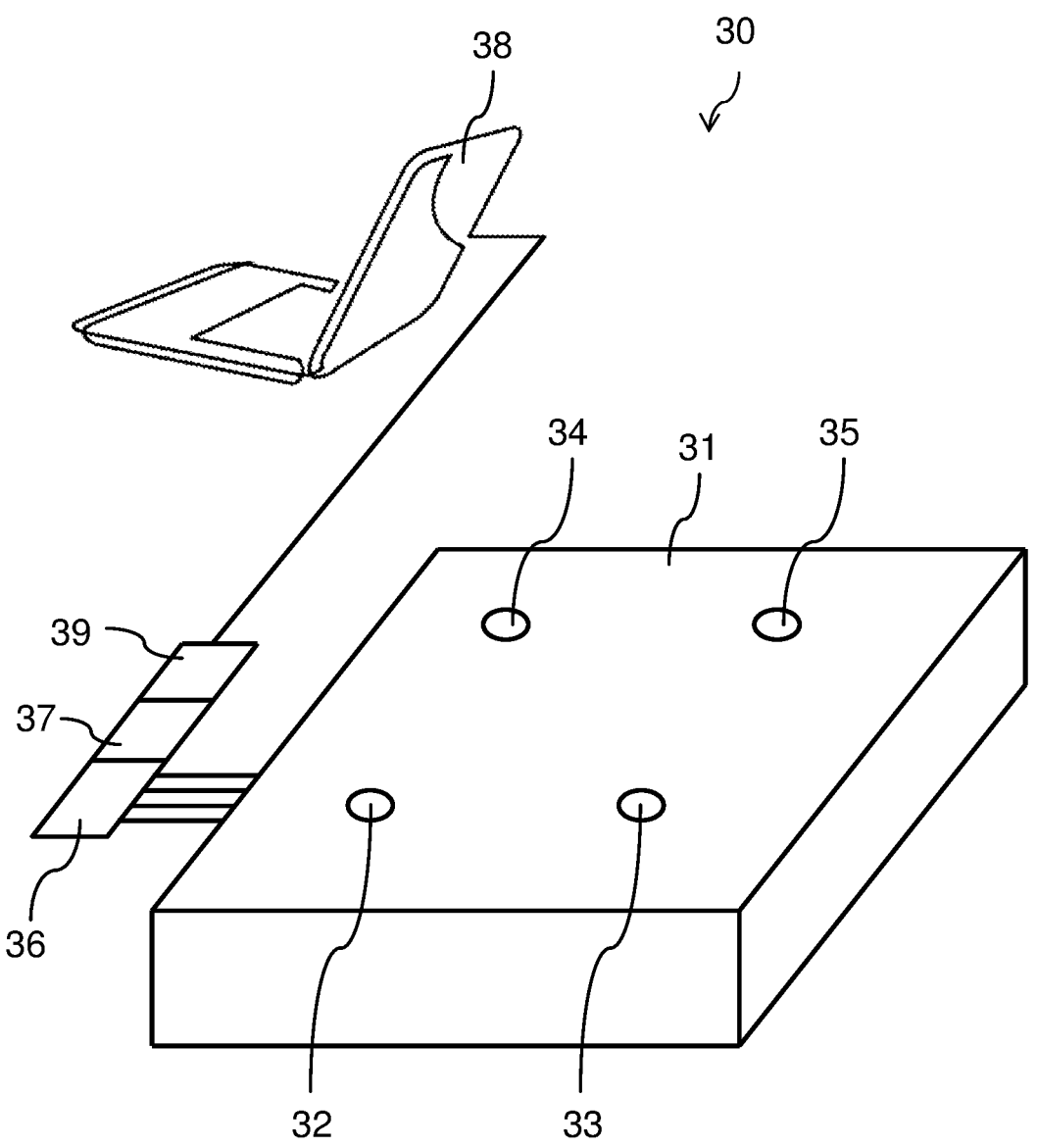
FIG. 1 represents, schematically, a particular embodiment of the device that is the subject of the invention.

FIG. 1 shows a schematic view of a first embodiment 30 of a device that is the subject of the present invention.

FIG. 1 shows a support 31 for a person (not shown), sensors 32 to 35 arranged in or on the support 31, a front-end electronic circuit 36 conditioning and amplifying the signal from the sensors 32 to 35, an analogue-to-digital converter 37 converting data from the circuit 36, a microcontroller 39 and a computer 38 for processing the data.

Figure 2:
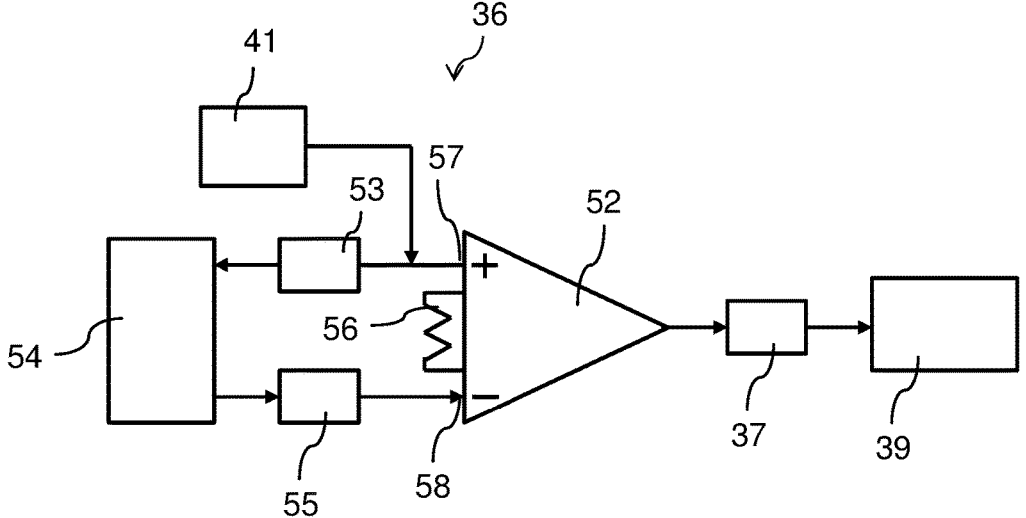
FIG. 2 represents, schematically, a front-end electronic circuit conditioning the signal from the sensors.

The support 31 is, for example, a bed, mattress, cushion or seat. The sensors 32 to 35 are, for example, pressure sensors, possibly in the form of matrices as described below, or accelerometers. A particular embodiment of the circuit 36 is shown in FIG. 2. The data processing computer 38 performs, for example, cardiac or chest mapping of the person, as a function of the digital signals coming from the analogue-to-digital converter 37, according to known algorithms.

The front-end circuit 36 identifies the resonance frequency of the system, filters the drift of the direct component and the damping noise, and greatly amplifies the signal without saturation, or with a reduced saturation time, after the patient's movement. In the embodiment shown in FIG. 2, the front-end circuit 36 comprises a multiplexer 41 of the analogue signals coming from the sensors 32 to 35, followed by an instrumentation amplifier 52 whose output is connected to the analogue-to-digital converter 37. The amplifier 52 has a very high gain, for example higher than 10, or even 100. The analogue-to-digital converter 37 is preceded by an anti-aliasing filter incorporated in the analogue-to-digital converter 37.

The multiplexed signal from the multiplexer 41 is supplied to an input (here the positive input 57) of the amplifier 52 and to an analogue-to-digital converter 53. A digital filter 54 filters the digitized signal and a digital-to-analogue converter 55 converts the digitally filtered signal and delivers it to the other input (here the negative input 58) of the amplifier 52. A resistor 56 controls the gain of the amplifier 52, between the inputs of the operational amplifier 52.

The digital signal processor (or DSP), which realizes the digital filter 54 is a 32-bit STM32L476 (registered trademark), mounted on a Nucleo-L476RG (registered trademark) board, for which the channels of the analogue-to-digital converters (or ADC) and digital-to-analogue converters (or DAC) have a resolution of 12 bits and a sampling frequency fs between 128 and 512 Hz, for example 256 Hz per sensor.

The frequency of the multiplexer is therefore N×fs, at least 130 kHz to achieve the minimum spatio-temporal resolution for 1024 sensors (fs=128 Hz and N=1024 sensors) and up to 2 MHz for the maximum spatio-temporal resolution (fs=512 Hz and N=4096 sensors). The resolution of the quantizer is 8 to 16 bits, typically 12 bits.

The microcontroller 39 demultiplexes the filtered signals on output from the analogue-to-digital converter 37 and conditions these signals into a matrix then sends them to the computer 38. The computer 38 next displays the matrices in the form of a video, and then possibly compresses these matrices. The ARM MBED (registered trademark) operating system has been used with the DSP library of CMSIS (registered trademark). A Universal Serial Bus (or USB) is used for the serial communication with a computer and the supply of the circuit.

The sensor is an LIS344ALH (registered trademark) accelerometer with a low noise density of 50 μg/√Hz and high sensitivity of 0.66 V/g. It is mounted on a STEVAL-MKI015V1 (registered trademark) evaluation board, and the FS, PD and ST pins are grounded. It is powered by a single 3.3V supply and measures accelerations of +/–2 g in this configuration. It is oriented so that the Z axis is in the direction of gravity.

The front-end mixed circuit 36 conditioning signals has a mixed signal architecture, i.e. a topology where an analogue signal is digitized by an ADC analogue-to-digital converter, filtered by a DSP (Digital Signal Processor) and then synthesized by a DAC digital-to-analogue converter. Such circuits have the same advantages as the digital filters, for example a frequency band with a clear transition or a very reduced stabilization time, and can be associated with an analogue amplifier.

In the case of the BCG, the undesirable components of the analogue acceleration signals must be filtered before amplification and digitization. The architecture developed, shown in FIG. 2, eliminates these undesirable components and amplifies the resulting signal using an instrumentation amplifier.

The resulting signal is expressed by equation 1, where G is the gain of the amplifier, and f is the digital filter.

$$V_{out}=G\cdot[\text{Vin}-f(\text{Vin})] \quad \text{(equation 1)}$$

During the return signal synthesis, a saturation is utilized to respect equation 2.

$$0<G\cdot[\text{Vin}-f(\text{Vin})]+\text{Vref}<3.3 \quad \text{(equation 2)}$$

Development and utilization of the digital filters: to eliminate the undesirable components of the signal, two types of linear digital filters have been utilized in embodiments of the device that is the subject of the invention. It consists of finite impulse response (FIR) filters and infinite impulse response (IIR) filters of the second order, shown in FIG. 3 and generally known as "cascade of biquad filters". The FIR filters and biquad filters are respectively defined by equation 3 and equation 4, where n is the sampling index, x and y are the input and output signals, N is the number of coefficients, and {a_n} and {b_n} are the feedback and reaction coefficients.

$$y[n] = b_0 \cdot x[n] + \cdots + b_{N-1} \cdot x[n-N+1] \quad \text{(equation 3)}$$

$$y[n] = b_0 \cdot x[n] + b_1 \cdot x[n-1] + \quad \text{(equation 4)}$$

$$b_2 \cdot x[n-2] + a_1 \cdot y[n-1] + a_2 \cdot y[n-2]$$

By convention, $a_0$ is set to 1.

Figure 3:
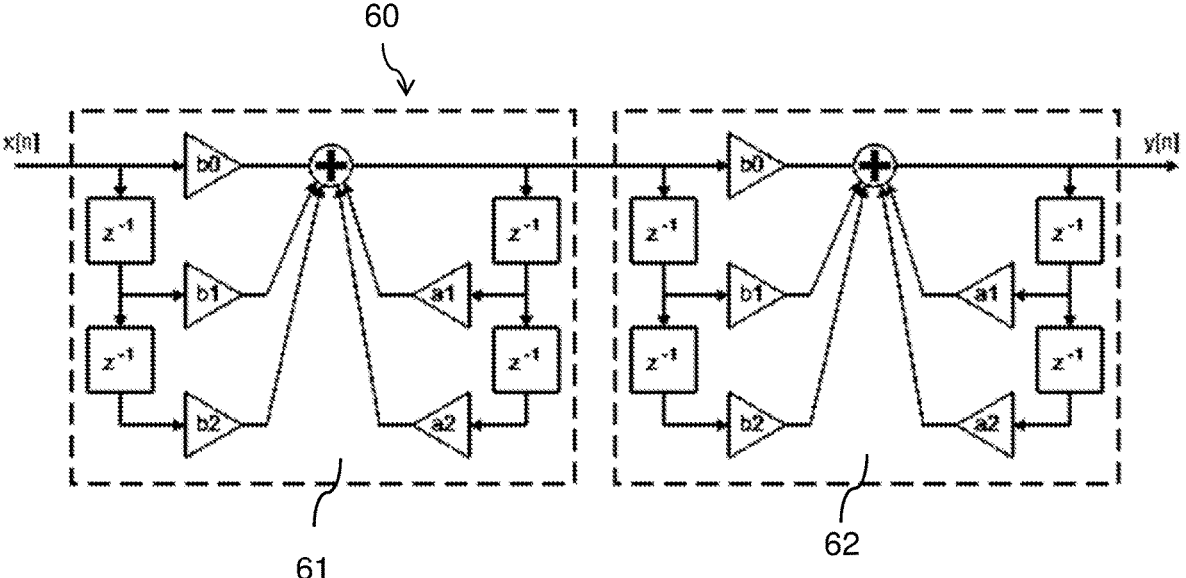
FIG. 3 represents, schematically, an example of a fourth-order IIR filter.

FIG. 3 shows an example of a fourth-order IIR filter 60, a cascade of two biquad filters 61 and 62, as implemented by the DSP library of CMSIS.

The filter's coefficients are calculated using the Python scipy.signal (registered trademarks) library on a 64-bit computer. They must be quantized to 32-bit coefficients before being implemented on the processor processing the DSP signal, which can generate errors, in particular for the IIR filters having filters with strong constraints and a very low cutoff frequency. For example, FIGS. 4 and 5 show the quantization of the poles for a second-order Butterworth filter with a cutoff frequency of 0.05 Hz and a sampling rate of 256 Hz.

Figure 4:
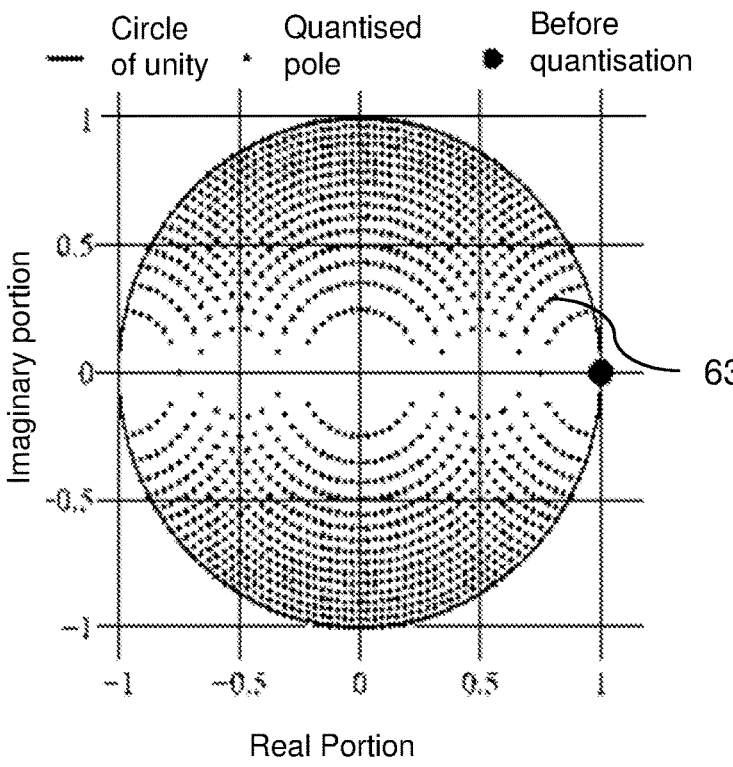
FIG. 4 represents a distribution of the poles of an IIR filter quantized on six bits.

In FIG. 4, the distribution of the poles 63 quantized on six bits is shown on a horizontal axis representing their real portion and a vertical axis representing their imaginary portion.

Figure 5:
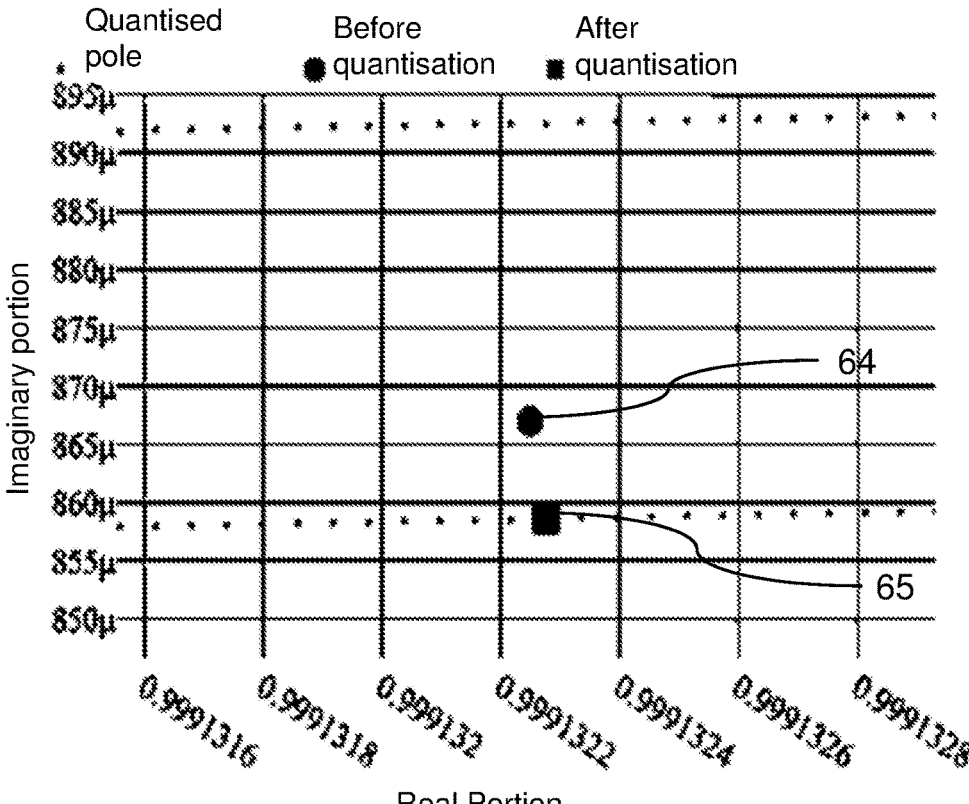
FIG. 5 represents a quantization of a pole of an IIR filter quantized on 64 bits to 32 bits.

FIG. 5 shows the quantization of a 64-bit pole 64, before quantization, into a 32-bit pole 65, after quantization. Each of these poles is shown on a horizontal axis representing its real portion and a vertical axis representing its imaginary portion.

Figure 6:
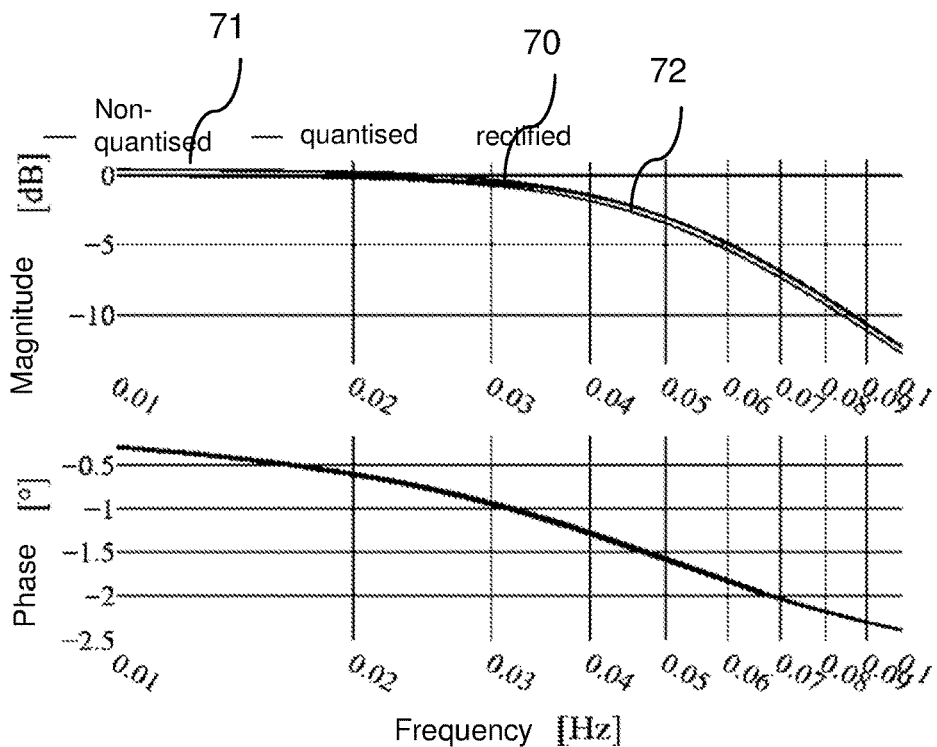
FIG. 6 represents, in the form of a frequency function curve, an effect of the quantization and rectification of the pass-band of an IIR filter.

This coefficient quantization is likely to modify the frequency response of the filter, for example the pass-band gain as shown in FIG. 6 using the same filter as FIGS. 4 and 5. After quantization, the pass-band gain has been systematically corrected to 0 dB using equation 5.

$$b'_n = b_n \frac{\sum a_i}{\sum b_j} \quad \text{(equation 5)}$$

FIG. 6 shows, with a horizontal axis representing the frequencies and two vertical axes representing, on top, the amplitudes and, below, the phases, a non-quantized signal 70, a quantized signal 71 and a rectified signal 72. FIG. 6 therefore shows the effect of the quantization and rectification of the pass-band.

The stabilization time of the filters depends on the initialization. The state of the filter is generally initialized to zero: the signal is therefore causal. However, the sensor has a rest position that is known or can be estimated. In the case of the accelerometer described already, it can be assumed that it is placed flat on the mattress, which is itself horizontal: the z axis should see an offset value of approximately +1 g, i.e. 2.31 V in this setting mode. The filter is initialized by considering that the signal is 2.31 V before beginning the recording.

With regard to the elimination of the drift of the direct component, this represents an often-undesirable component of the physiological signal. This is a low-frequency component that does not allow a high-gain amplification. In ballistocardiography, the movement of the direct component is a voltage offset dependent on the position of the body and weight in the bed. For example, during a change of position by the patient, the orientation of the accelerometer and the projection of gravity on the axes of the accelerometer change. The inventors have observed that this offset value is generally located between 0.1 and 0.5 g, for which the amplifier would be saturated with G>3 dB.

Breathing, for which the frequency varies from 0.5-1.0 Hz in neonatology up to 0.1 Hz in geriatrics, can be considered either as a portion of the drift of the direct component, or as a useful component of the signal. In the embodiment described here, the breathing is not filtered, and consequently the cutoff frequency of the basic filter is set at 0.05 Hz and f is a low-pass filter (Equation 1).

In the case of the FIR, the window method is applied using a Kaiser window with a minimum attenuation of 40 dB in the pass-band and a transition band width of 0.1 Hz. The resulting FIR filter has 5716 coefficients.

In the case of the FIR, a second-order Butterworth filter, chosen because of its maximum flat response in the pass-band, is developed and repeated twice in order to accentuate the transition. In the embodiment described here, the filter chosen is a fourth-order IIR filter, because the FIR filter is costly in calculations for the microcontroller 54.

Figure 7:
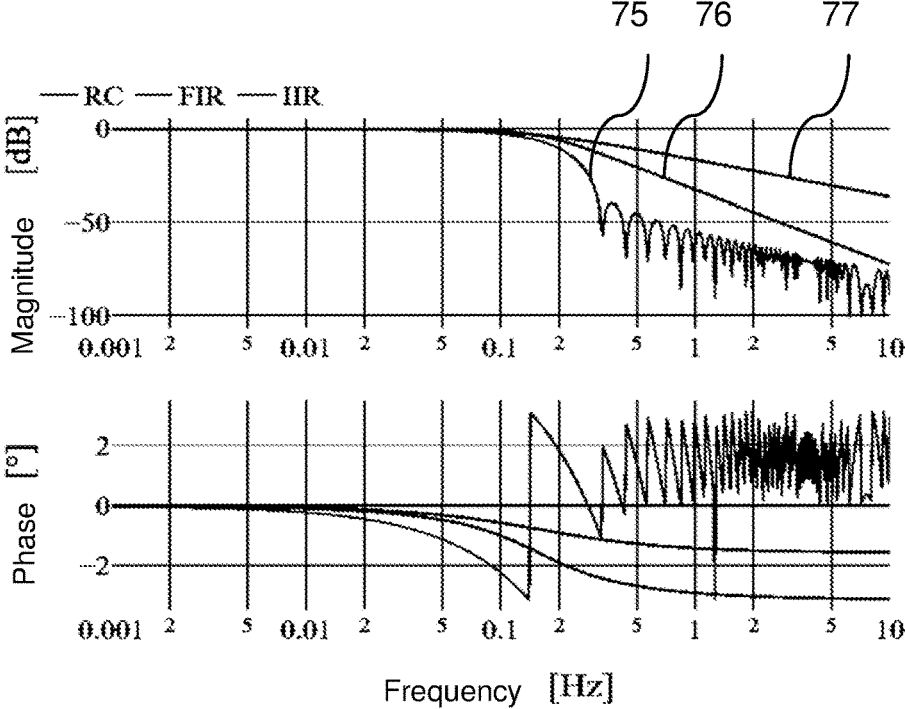
FIG. 7 represents frequency responses of the equivalent low-pass of the filters developed and the standard analogue RC filter.

FIG. 7 shows the responses of the FIR and IIR filters developed in equivalent low-pass. They are compared to a typical first-order resistor-capacitor (RC) filter with the same cutoff frequency.

FIG. 7 shows the frequency responses of the equivalent low-pass of the FIR filter, response 75, IIR filter, response 76 and a typical analogue RC filter, response 77. Note that the axes are identical to those in FIG. 6, but with a broader frequency range.

A gain of 21 dB is set in this embodiment. Lastly, the equivalent high-pass filter has the following numerator and denominators in table 1. It is defined by equation 6, equation 7 and equation 8.

$$V_{out} = g(V_{in}) \qquad \text{(equation 6)}$$

$$a'_n = a_n \qquad \text{(equation 7)}$$

$$b'_n = G \cdot (a_n - b_n) \qquad \text{(equation 8)}$$

| a0 | 1 |
| --- | --- |
| a1 | −1.9982646 |
| a2 | 0.99826604 |
| b0 | 11.183295 |
| b1 | −22.3472 |
| b2 | 11.163904 |

Numerators a0, a1 and a2 and denominators b0, b1, b2 of the equivalent high-pass filter.

Figure 8:
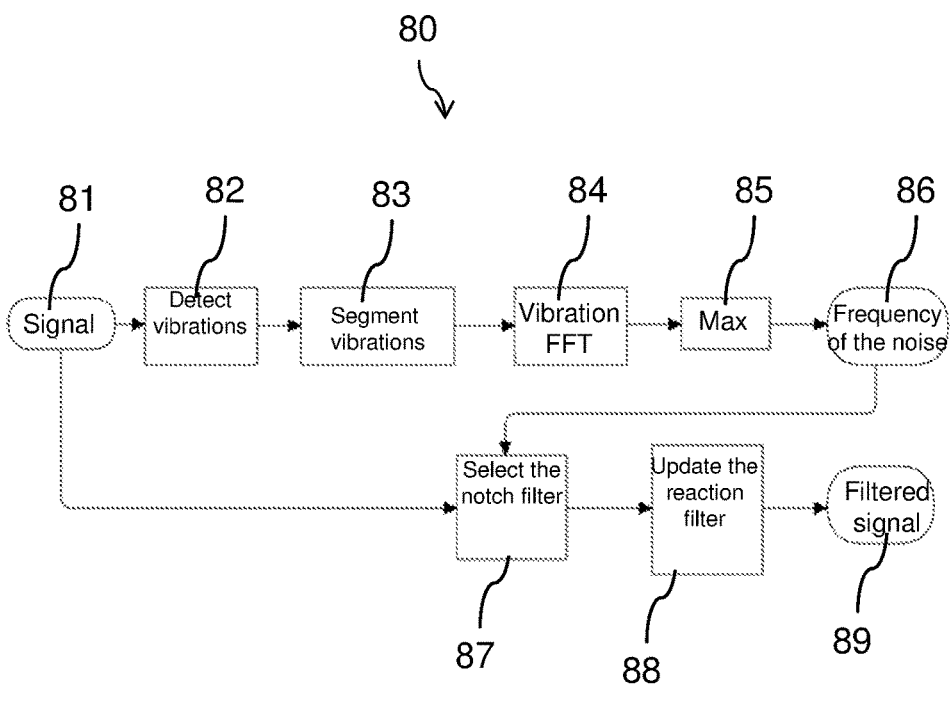
FIG. 8 represents steps of a pseudoalgorithm for identifying and filtering the frequency of the noise.

With regard to the identification and filtering of noise frequencies, the frequency of the noise is identified and filtered using the built-in algorithm 80 shown in FIG. 8.

FIG. 8 shows an input 81 of the amplified signal, a vibration detection step 82, a vibration segmentation step 83, a Fast Fourier Transform (or FFT) step 84, a maximum extraction step 85 that provides the frequency of the noise 86, a notch filter selection step 87, a step 88 of updating the reaction filter, and a step 89 of outputting the filtered signal.

The step 82 of detecting vibrations is parameterized by a voltage limit value, hereinafter referred to as a "threshold", beyond which the vibration is detected. The vibration begins when the amplified signal exceeds this voltage limit value, and has a duration considered fixed.

The power spectral density of the segmented vibration is calculated by the microcontroller. Its peak is located at the frequency of the noise, such that it is located outside the BCG range of frequencies, otherwise the heartbeats could be deformed or filtered.

Several notch filters, with quality factors Q=0.707, have been calculated first using the scipy.signal library outside the microcontroller. The notch filter whose frequency is closest to the frequency of the noise is selected, and added to the IIR basic filter.

In this section, the results of the experiment are detailed: the filtering of the drift of the direct component, the comparison of the stabilization time, and the identification and filtering of the noise are analysed. The raw signals presented are not post-processed.

Filtering the Direct Component

Figure 9:
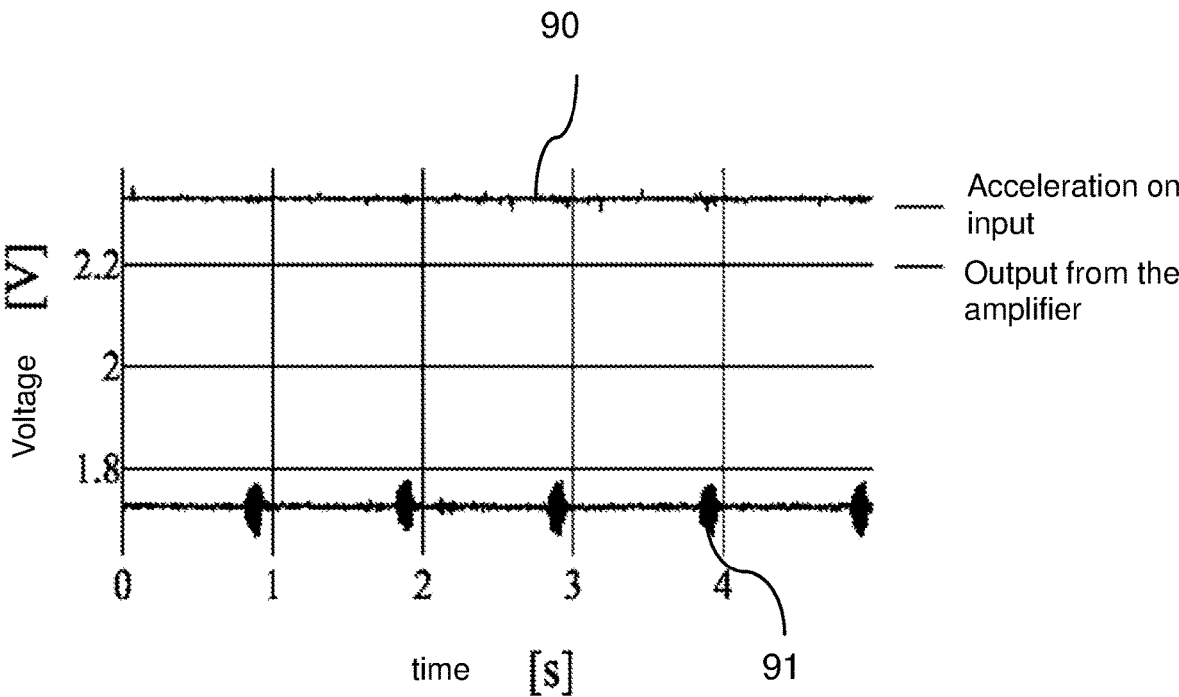
FIG. 9 is an illustration of the elimination of the drift of the direct component with an amplification of 21 dB.

The IIR filter successfully filters the direct component, and this is eliminated by the amplifier. In the balance state, the maximum peak-to-peak amplitude of the impulsions is ten times higher on output than on input. FIG. 9 is an illustration of the signal before and after the amplifier with an impulsion amplitude lower than the noise level, with an amplification of 21 dB.

FIG. 9 shows a sensor output curve 90 and an amplified acceleration curve 91. The horizontal axis represents the time in seconds, and the vertical axis represents the voltage. It can be seen that a pulse, with a frequency of approximately 60 hertz, is extracted from the initial noised signal, despite the defects of the initial signal.

Figure 10:
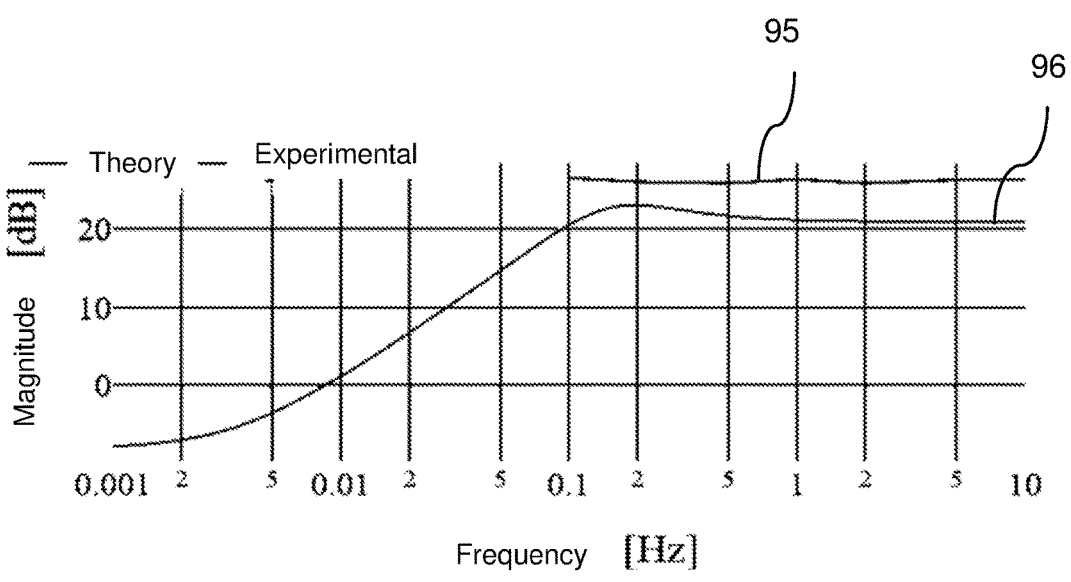
FIG. 10 represents a comparison of the frequency responses for a gain of 21 dB, IIR quantized relative to experimental points.

This filter makes it possible to generate vibrations at different constant frequencies and compare the accelerations measured before and after the filtering and the amplification by their average quadratic values. The frequency response 95 measured experimentally is compared with this filter's theoretical response 96, in FIG. 10, for the quantized IIR filter, with a gain of 21 dB.

Comparing Stabilization Times

Figure 11:
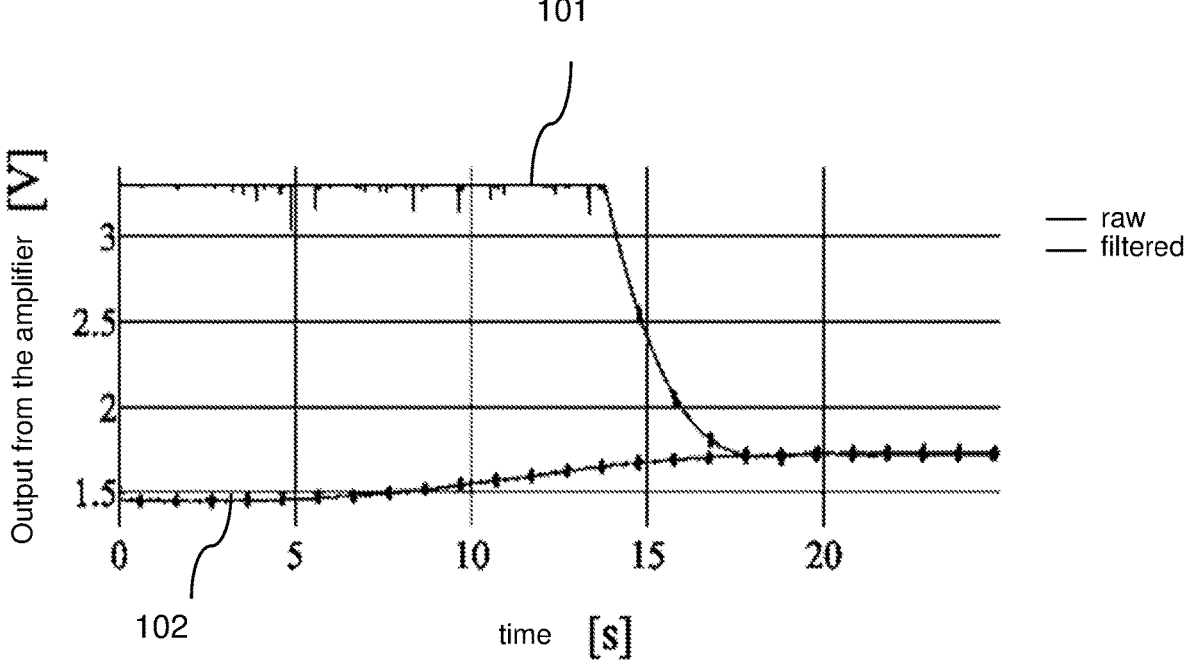
FIG. 11 represents an effect of the initialization of the state of the filter over the stabilization time.

The signals have been recorded at different levels of initialization. FIG. 11 is a superimposition of two signals at different times, with an offset initialization of 0 V, curve 101, and 2.31 V, curve 102. It can be seen that, when the filter state is initialized to 0 V, the amplifier can saturate for tens of seconds, which is not the case if the offset is well estimated.

Figure 12:
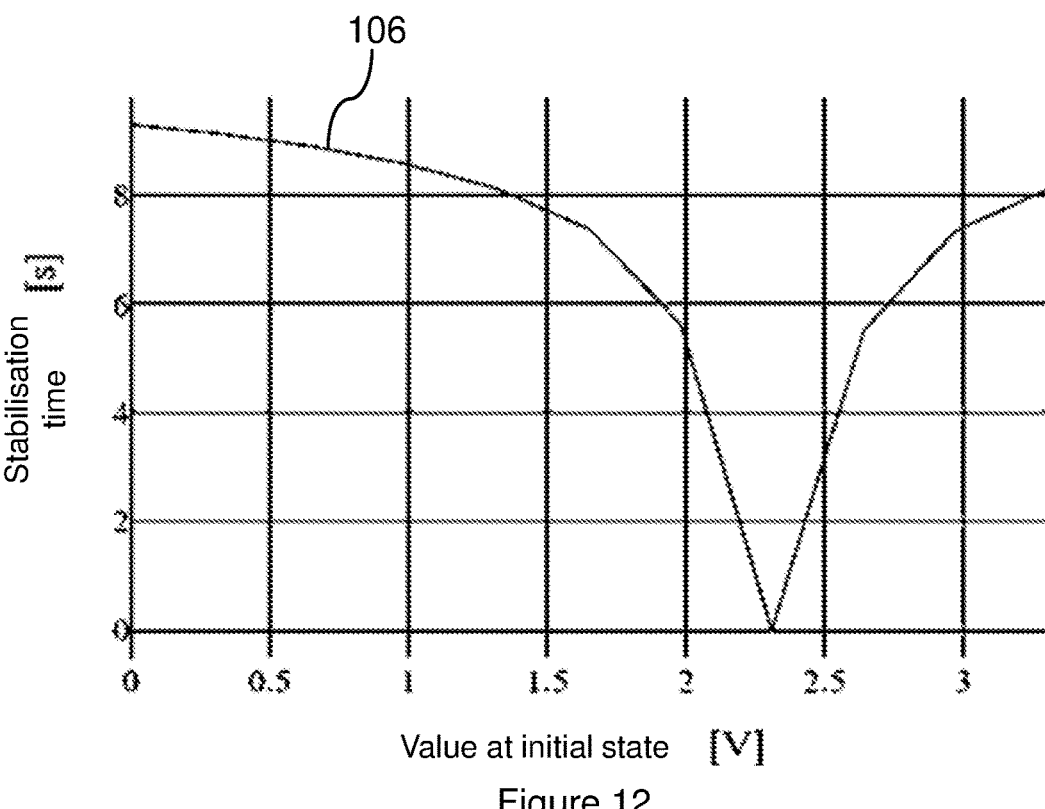
FIG. 12 represents a stabilization time for different initializations of the state of the filter with an amplification of 21 dB.

The stabilization time, on the y-axis, depends on the initialization of the offset, on the x-axis, as shown by curve 106 in FIG. 12, with an amplification of 21 dB.

Identifying Noises

Figure 13:
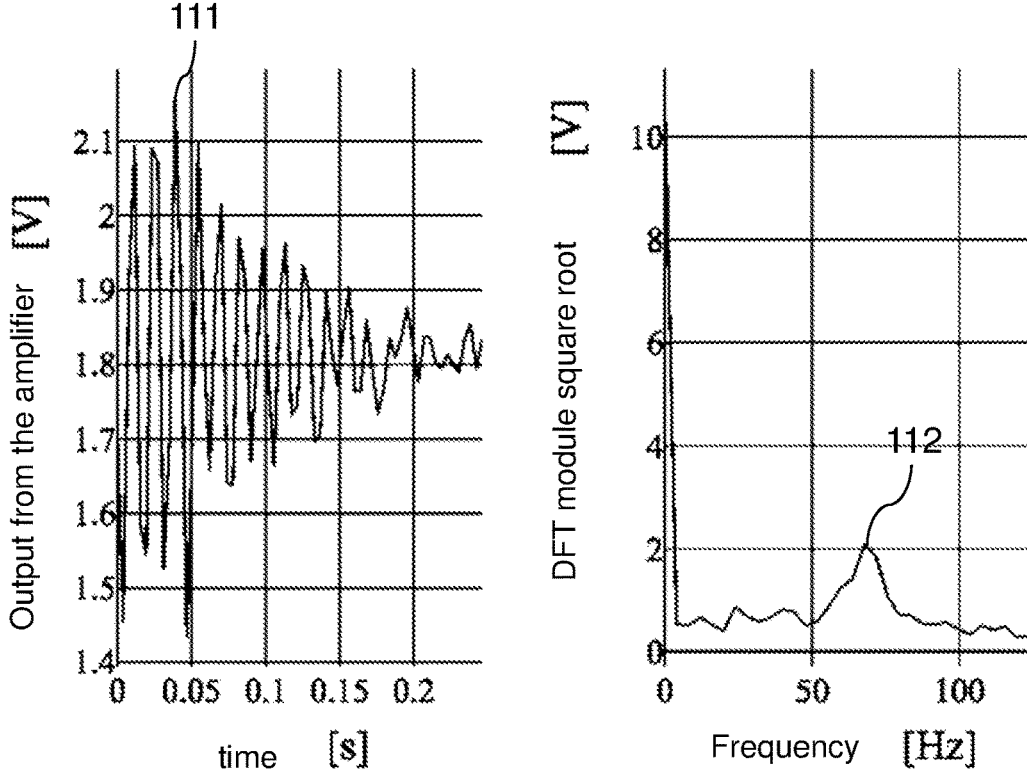
FIG. 13 represents an example of a BCG impulse and its single-sided frequency spectrum calculated by a microcontroller.

The threshold and duration have been set respectively to 1.5% and 0.25 s of the drift of the initial direct component. The noise was generated by pulsed vibrations, i.e. the simulated BCG. The frequency 112 of the noise 111 determined by the microcontroller is approximately 68 Hz, as can be seen in FIG. 13. This is the resonance frequency of the damping system.

A notch filter has then been selected by the algorithm illustrated by FIG. 8 to filter the noise frequency identified.

In conclusion, the present invention utilizes a new front-end signal conditioning circuit which identifies the resonance frequency of the system, filters the drift of the direct component and the damping noise, and amplifies the BCG signal without saturation after the patient's movement.

In the above description, the amplification gain is 21 dB for illustrating the principle of the BCG front-end circuit. However, the invention is not limited to this level of gain, especially when a specific electronic circuit with an adequate ground plane is used.

Relative to the normal BCG instruments, this front-end conditioning circuit described above has a smaller stabilization time and a sharper frequency transition. It opens up possibilities of medical applications, in real time and at low cost.

The incorporation of this front-end circuit in a BCG device is described below. It is noted that the frequencies of 0.05 Hz to 25 Hz comprise the heart and respiratory phenomena.

The aim of this device is to establish a cardio-respiratory mapping of the body surface by time-division multiplexing of an analogue filter with a digital feedback loop.

A mixed filter configuration 36 as described above replaces an analogue configuration in the feedback loop of an operational amplifier, referred to as "digital feedback".

This "digital feedback" makes it possible to increase the constraints of the filter, to digitally initialize it so that it is more rapid, to attenuate an ambient noise whose pass-band changes over time, and to carry out high-frequency time division multiplexing of low cutoff frequency filters.

The system is a BCG imaging system that comprises the following elements:

A surface sensor for the body pressure;

An acquisition unit with time division multiplexing of a filter and an amplifier;

A digital signal processing software system.

The surface sensor for the body pressure is normally used for measuring an individual's comfort in a lying or seated position, and/or the risks of pressure sores. It is generally comprised of several modules of size 35×40 cm to 50×100 cm, with resolutions ranging from 0.5 to 1 sensor/cm2, i.e. N=1024 to 4096 sensors per module. Example of "Body Pressure Measurement Systems" from Tekscan (registered trademark).

An acquisition unit is utilized for each module, i.e. for more than a thousand pressure sensors.

The filter, linear or non-linear, can be parameterized by its pass-band, transition width, maximum attenuation in pass-band and minimum attenuation in cutoff-band. The amplifier has a parameterizable gain. The filter and the amplifier can be parameterized in real time, for example for amplifying a signal or attenuating a noise whose pass-bands change over time.

Where fs is the sampling frequency of the signal. For measuring the cardiac function, the pass-band of the filter is configured to [1; fs/2] and the gain from 7 to 40 dB (×5 to ×100). For measuring the respiratory function, the pass-band of the filter is configured to [0.1; 1] and the gain from 7 to 40 dB. For measuring both functions simultaneously, the pass-band of the filter is configured to [0.5; fs/2] and the gain from 7 to 40 dB. In both cases, the direct component of the signal must be removed so that the amplifier is not saturated (AC coupling).

The analogue-to-digital converter comprises an anti-aliasing filter with cutoff frequency fs/2.

The sampling frequency of the signal fs is comprised between 128 and 512 Hz, the frequency of the multiplexer is therefore N×fs, at least 130 kHz to achieve the minimum spatio-temporal resolution (fs=128 Hz and N=1024 sensors) and up to 2 MHz for the maximum spatio-temporal resolution (fs=512 Hz and N=4096 sensors).

Lastly, the resolution of the quantizer is 8 to 16 bits, typically 12 bits.

In order to rapidly multiplex a filter with a pass-band so slow, an operational amplifier with a digital feedback loop is used.

An advantage of the configuration illustrated in FIG. 2, in which the pass-band of the filter is subtracted from the signal Vin by the amplifier, is that the filter is a digital filter executed on a microcontroller, preceded by an analogue-to-digital converter and followed by a digital-to-analogue converter. It can be of any order whatsoever, finite or infinite impulse response, linear or non-linear, or adaptive.

In addition, the state of the filter can be initialized such that the amplifier saturates for a shorter time, as if the capacitor of an analogue filter was pre-charged at its balance value.

Lastly, the state and output of this filter can be stored at each sampling step in a memory: it can therefore be time division multiplexed, even if the frequency is much larger than the cutoff frequency of the filter. In addition, the digital filter in the feedback loop makes it possible to remove the frequency bands of the noise to prevent the latter from saturating the amplifier.

The digital signal processing software can be embedded on the acquisition board for real-time processing or on a computer for post-processing. It interpolates the measurements for digitally increasing the resolution of the image and enables the clinician to view the cardiac and respiratory functions, and quantizes these functions (breathing and heart rates, direction of the pulse wave, etc.).

This unit has many advantages. In hospitals, it enables examinations of cardiac and respiratory functions to be performed simply and quickly, by being directly built into the bed. At home or in non-medical environments, it makes it possible to carry out long- and short-term monitoring of vital data (bed, chair, seat, clothing).

It has the same advantages as the known types of ballistocardiography systems:

it is not very sensitive to layers of clothes or sheets, compared to other measurement systems, e.g. by Doppler ultrasound or CCD camera.

it allows the cardiac and respiratory functions to be measured simultaneously.

It has other advantages than the known ballistocardiography systems:

it carries out a surface measurement with a high resolution (>1000 points), it is more robust thanks to the active attenuation of the noise, and therefore easier to use in a noisy environment, it is more rapid thanks to the initialization of the digital filter.

In addition, its acquisition unit is simple, compact and not very expensive.

In some embodiments, the instrumentation amplifier used is an AD623AN (registered trademark), whose gain is adjustable thanks to a resistor. In experiments, two gains are used: a unity gain (no resistor, circuit open) and a gain ×10 (resistor of approximately ten kΩ). The results presented below are valid for a gain ×100 with a stabilized power supply and an adequate ground plane.

In FIG. 8 and following figures, a processing of signals coming from accelerometers is described. Except for the units and values, these signals are similar to the signals coming from pressure sensors, with, in particular, a direct component, noise and physiological signals to be extracted.

In some examples of implementation, the output from the accelerometer is filtered on the Nucleo (registered trademark) board, thanks to the MBED-DSP library, and in particular the functions arm_fir_f32( ) and arm_biquad_cascade_df1_f32( )

Development of the Filters

Two types of filters are studied:

FIR filters

IIR filters.

They are developed with the scipy.signal library from Python.

The FIR filter order is numTaps−1 and the filter consists of numTaps coefficients {bi}.

$$y[n]=b[0]^*x[n]+b[1]^*x[n-1]+b[2]^*x[n-2]+\ldots+b[numTaps-1]^*x[n-numTaps+1]$$

The FIR filter is calculated by the window method, with an optimum Kaiser window. This is determined with as constraint an attenuation of 40 dB in the pass-band and a transition of the order of 0.1 Hz (Nyquist frequency 128 Hz):

numtaps,beta=scipy.signal.kaiserord(40,0.1/128)

The number of coefficients of this optimum window is 5716. With the pass-band constraints (cutoff frequency 0.05 Hz), the following are obtained:

b=scipy.signal.firwin(numtaps=numtaps,cutoff=0.05,
Windows=('kaiser',beta),pass_zero=True,
fs=256).

The biquad IIR filter, first-order Butterworth, is second-order and contains a denominator. For an equivalent transition width and an equivalent attenuation, the IIR filter order is much lower than for the preceding FIR filter, but it can be less stable.

$$y[n]=b0^*x[n]+b1^*x[n-1]+b2^*x[n-2]+a1^*y[n-1]+a2^*y[n-2]$$

It is obtained by the following functions:

b,a=butter(2,0.05/(fs/2));

pCoeffs=concatenate((b,−a[1:]));

Note that the first-order Butterworth filter is interesting to study, because it concerns the digital equivalent of the analogue filter realized in the AC coupling electronic circuits (in alternating current): a capacitor followed by a resistor, possibly with an operational amplifier to address impedance issues or to add a gain.

In an IIR biquad cascade filter, sections of the preceding IIR filter are connected in series.

As described above, the 64-bit coefficients calculated on the computer must, in some embodiments, be quantized in 32 bits, and the filter's response varies enormously, as the stability margins are small. Consequently, some biquad filters developed using the 64-bit architecture are unstable under 32 bits.

Note that the number of coefficients is much lower for an FIR filter, thus the number of operations is much lower, which is favourable for the speed of processing signals. The structure of the filter can also be improved to further reduce the number of operations (type II structure) or to reduce the influence of the quantization of the coefficients (Gold & Rader structure).

Figure 14:
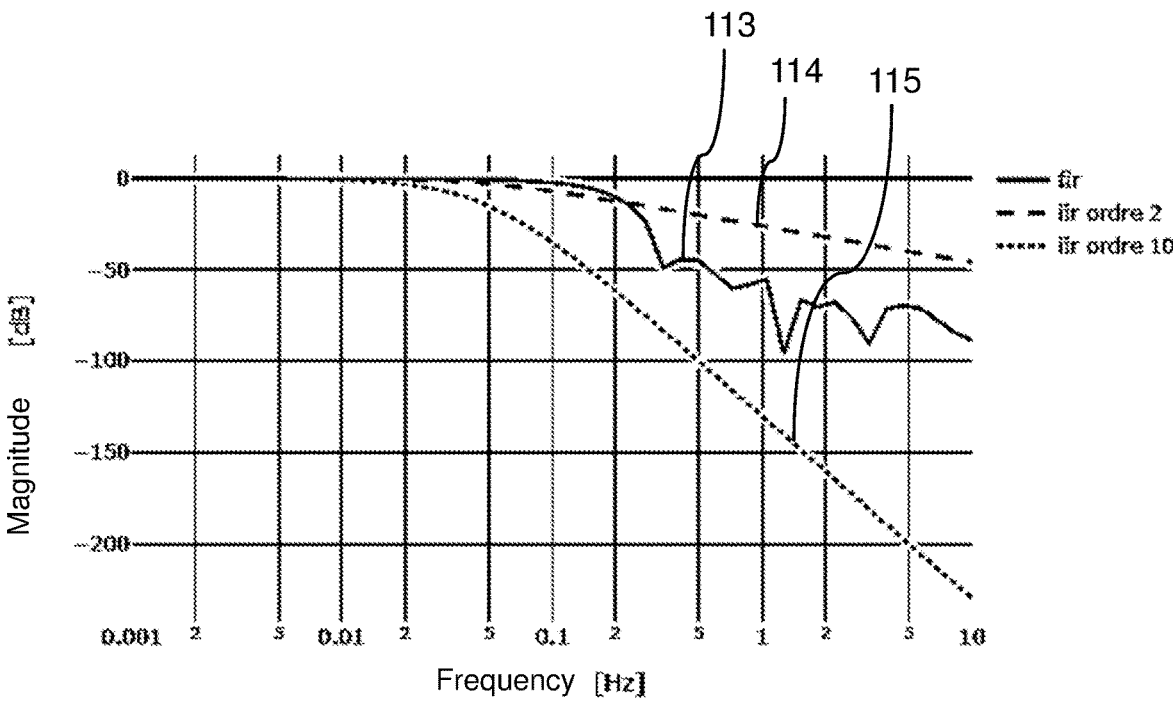
FIG. 14 represents, in amplitudes, the frequency response of different filters.
Figure 15:
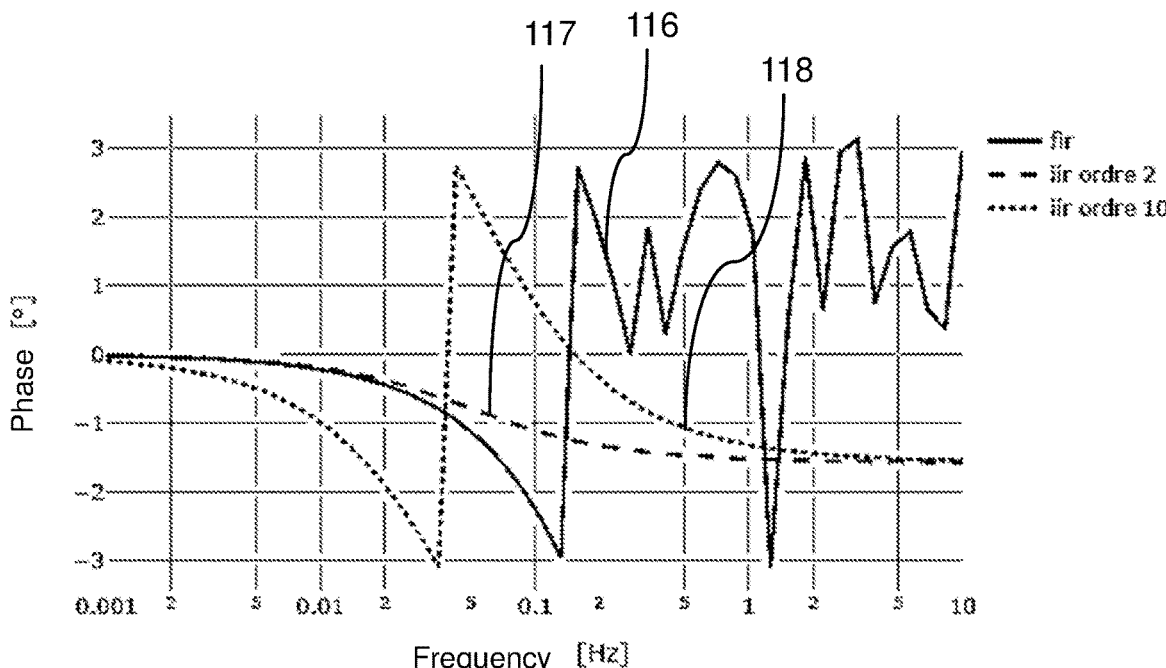
FIG. 15 represents, in phases, the frequency response of different filters.

FIGS. 14 and 15 show, in amplitudes and in phases, the frequency responses of different filters. The curves 113 and 116 show the response of an FIR filter. The curves 114 and 117 show the response of a second-order IIR filter. The curves 115 and 118 show the response of a tenth-order IIR filter. The advantages of using digital filters are clear (transition more abrupt, attenuation higher). The response of the second-order IIR filter is equivalent to that of a first-order analogue low-pass filter. Note that, in other embodiments, other filters are chosen, for example non-linear filters (median filter, wavelets, etc.), and also for uses other than AC coupling.

With regard to saturation, the AD623 amplifier is powered at 0-5 V, therefore its output voltage, in the event of saturation, can exceed the maximum voltage of the analogue-to-digital converter. It is necessary to add either saturation hardware on the output from the amplifier, or saturation software on the output from the digital-to-analogue converter. This second path presents advantages in terms of simplicity of utilization:

float expectedOutput=(rawSignal−filteredSignal)
*analogGain+Vref;
if (expectedOutput>3.3){
feedback.write((rawSignal+(Vref−3.3)/analogGain)/3.3);
} else if (expectedOutput<0){
feedback.write((rawSignal+Vref/analogGain)/3.3);
} else {
feedback.write (filteredSignal/3.3);
}

For the saturation to be correct, the voltage Vref and the gain need to be measured with precision: using a voltmeter for the first (1.69 V) and the resistance value for the second (11.9 kΩ, i.e. a gain of ×9.4).

The state of the filter is usually initialized to zero, i.e. all the values x[n] and y[n] for which n<0 are zero. The signal is therefore causal.

The sensor has a rest position that is known or can be estimated. For an accelerometer in ballistocardiography, it is assumed that it is placed flat on the mattress, which is itself horizontal: the z axis is therefore +1 g in direct current value. According to the technical data sheet of the LIS344ALH accelerometer, the output direct current value of the accelerometer is therefore 2.31 V. The state of the filter can be initialized by requiring the values x[n] and y[n] to be equal to 2.31 V for numTaps<n<0.

For other sensors, a rapid low-pass filter (higher cutoff frequency) can also be realized for estimating the direct current value of the accelerometer and filling the second long filter with these values.

FIGS. 16 to 19 show the time response of the filter and amplifier in each of the configurations mentioned above.

Figure 16:
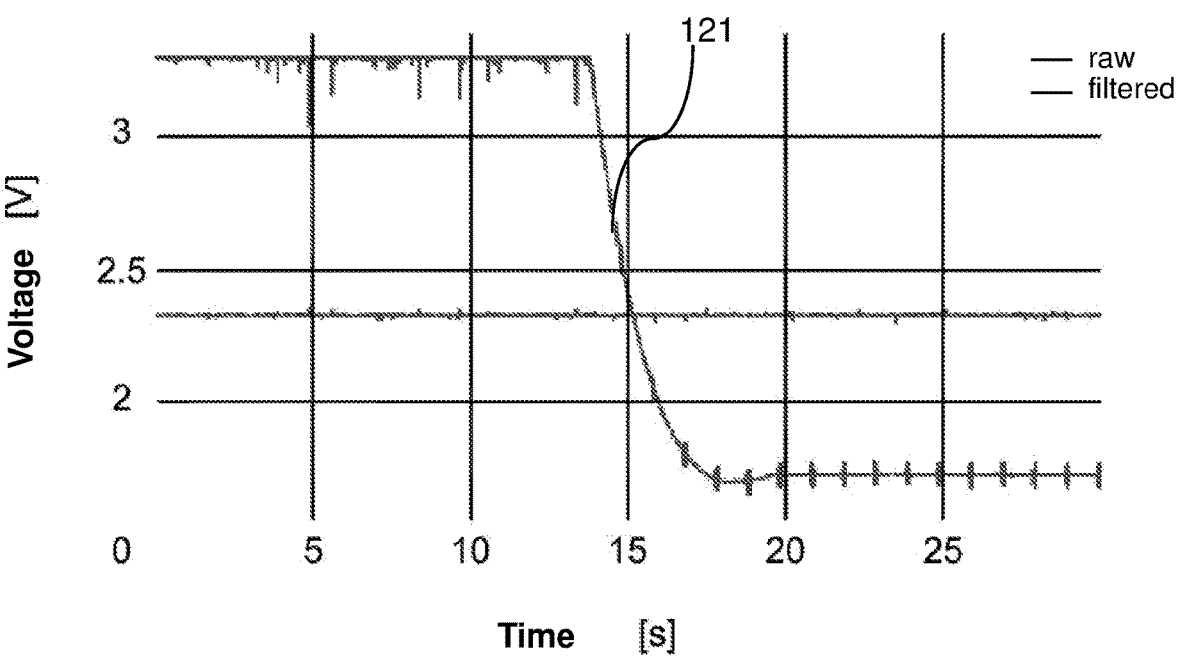
FIG. 16 represents the time response of the filter and amplifier in the FIR configuration.

FIG. 16 shows the response 121 of an FIR filter. The amplification of the impulsions (they are hidden in the noise of the raw signal, below the resolution limits of the ADC) are clearly seen, but the filter takes a certain time to load, which is inherent because the cutoff frequency is very low. This is also the case for the analogue filter and amplified when the gain of the amplifier is increased.

Figure 17:
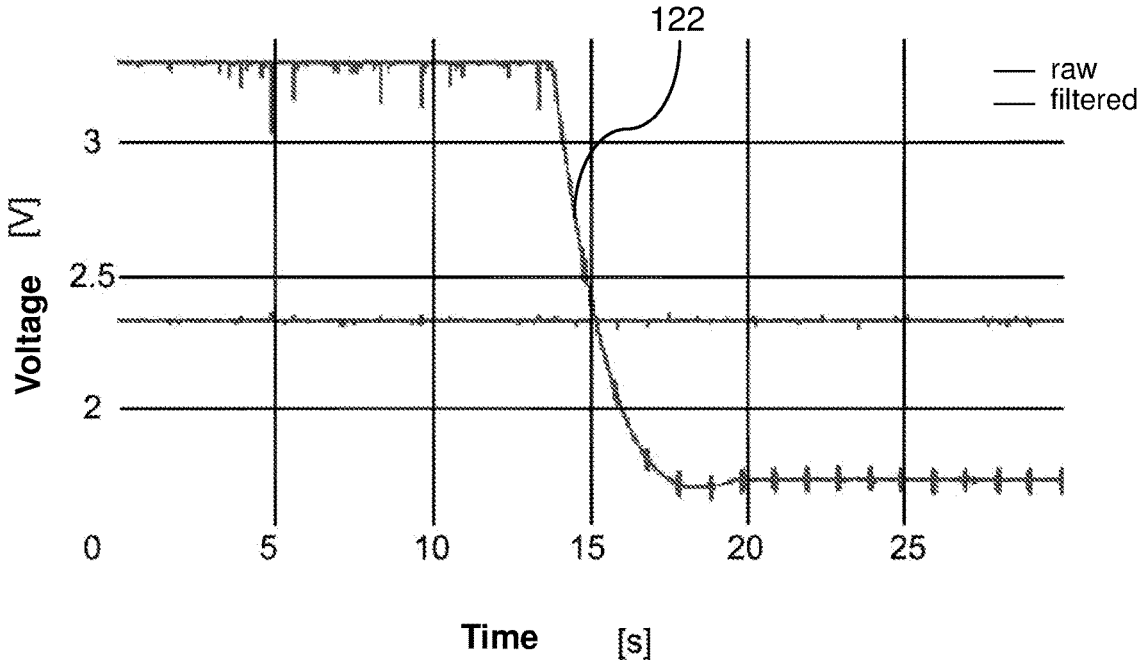
FIG. 17 represents the time response of the filter and amplifier in the single-section IIR configuration.

FIG. 17 shows the response 122 of a 1-section IIR filter. This filter has a behaviour identical to that of a first-order analogue high-pass circuit.

Figure 18:
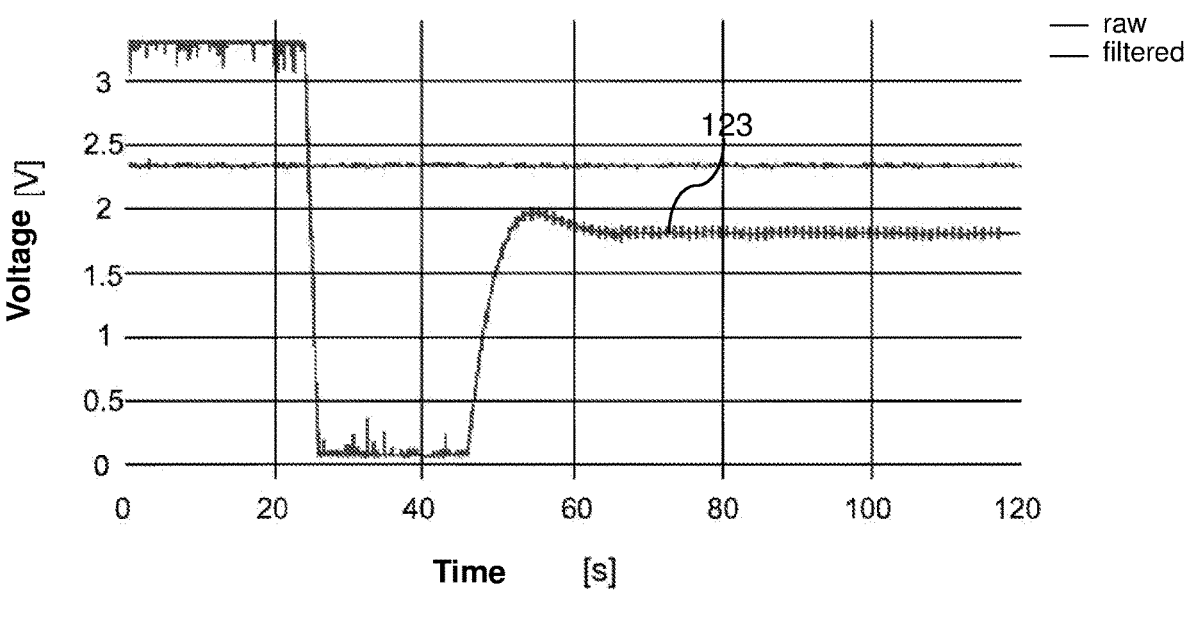
FIG. 18 represents the time response of the filter and amplifier in the five-section IIR configuration.

FIG. 18 shows the response 123 of a 5-section IIR filter. The time-scale is much longer, since there are more coefficients. There is not necessarily much interest in increasing the order of the IIR filter.

Figure 19:
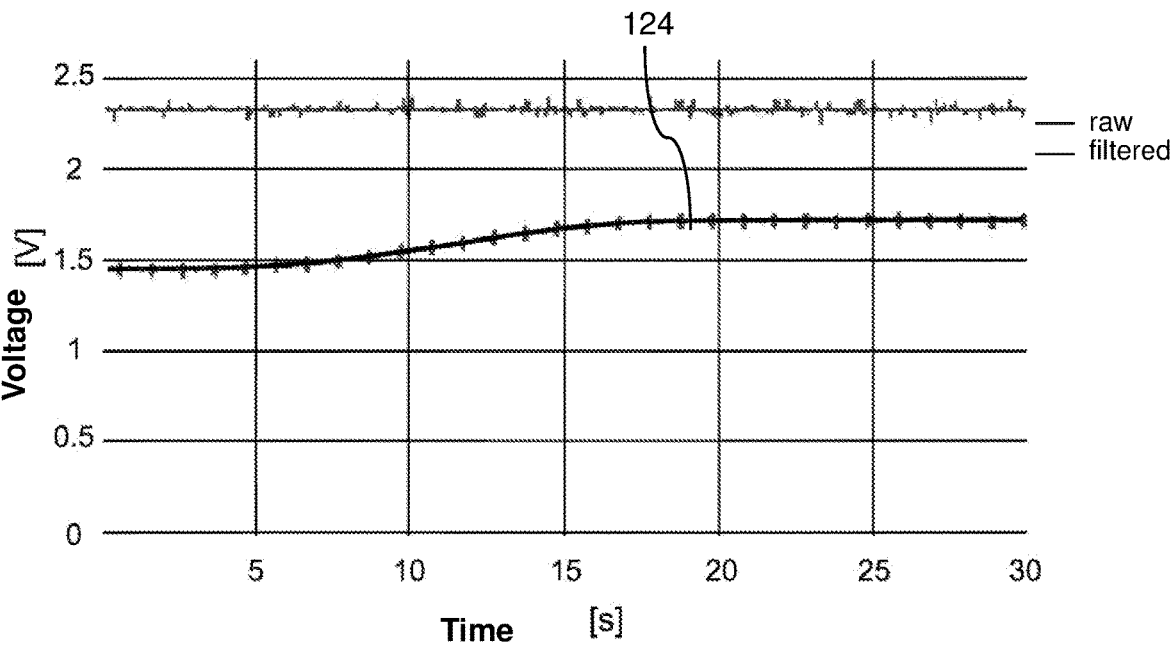
FIG. 19 represents the time response of the filter and amplifier in the FIR configuration with initialization of the state of the filter.

FIG. 19 shows the response 124 of an FIR filter with forced initialization. Logically, an absence of saturation is observed when the FIR filter is correctly initialized. This is one way of "pre-charging" the filter. A slight oscillation appears, which corresponds to the fact that the value of the direct component provided for the initialization of the filter is slightly different from the value of the real direct component of the accelerometer.

There is the same result of an absence of saturation when the filter is correctly initialized as with the IIR filters.

The present invention applies in particular to:

monitoring patients during a surgical operation; and/or viewing vital functions, for example viewing the pulse wave and contraction of the ventricles.

The invention claimed is:

1. A ballistocardiography device, comprising:

a support for a person;

a plurality of pressure or acceleration sensors each providing an analogue signal representative of a pressure or an acceleration measured at a point on the support or on the body of the person;

a multiplexer configured to receive a plurality of analogue signals from sensors and to output a signal successively representative of the input signals; and an operational amplifier having a first input connected to the output of the multiplexer and a second input connected to a mixed filter, and an amplified output for outputting an amplified signal, wherein said mixed filter includes an analogue-to-digital converter converting the output signal coming out of the multiplexer into digital data, a digital filter acting on the digital data and a digital-to-analogue converter converting the filtered digital data into an analogue signal, wherein said analogue signal is fed into said second input of the operational amplifier.

2. The device according to claim 1, wherein the digital filter is a cascade of biquad filters.

3. The device according to claim 1, wherein the sampling frequency of the analogue-to-digital converter is equal to the number of sensors multiplied by a number between 128 and 512.

4. The device according to claim 1, wherein the plurality of sensors forms at least one matrix of pressure sensors.

5. The device according to claim 1, wherein the gain of the amplifier is greater than 10.

6. Device for monitoring a patient during a surgical operation comprising the ballistocardiography device according to claim 1.

7. Device for viewing the pulse wave and the contraction of the ventricles comprising the ballistocardiography device according to claim 1.

8. A ballistocardiography method utilizing the device according to claim 1, which comprises the following steps:

a plurality of pressure or acceleration captures at different points of the support for a person providing, for each capture point, an analogue signal representative of a pressure or an acceleration measured at said point on the support or on the body of the person;

a multiplexing of the plurality of analogue signals; and an amplification of the multiplexed signal from which is subtracted a signal filtered by a mixed filter comprising an analogue-to-digital converter converting the signal coming out of the multiplexer into digital data, a digital filter acting on the digital data and a digital-to-analogue converter converting the filtered digital data into an analogue signal.

9. The method according to claim 8, which also comprises a step of estimating the direct component of the analogue signals, and a step of initializing the filter with the estimated direct component.

10. The method according to claim 8, which also comprises:

a step of detecting a vibration in the amplified signal;

a step of segmenting the vibration signal;

a step of transforming segments of the vibration signal in the frequency domain;

a step of obtaining a maximum of the vibration signal in the frequency domain;

a step of configuring a notch filter comprising the maximum obtained; and a step of filtering the amplified signal with the notch filter.

* * * * *